US00PP29545P2

(12) United States Plant Patent
Hartman

(10) Patent No.: US PP29,545 P2
(45) Date of Patent: Jul. 24, 2018

(54) ***CALADIUM* PLANT NAMED 'MESMERIZED'**

(50) Latin Name: *Caladium X hortulanum*
Varietal Denomination: Mesmerized

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 15/530,468

(22) Filed: Jan. 18, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Caladium* plant named 'Mesmerized', characterized by its intermediate height and upright plant habit; vigorous growth habit and rapid growth rate; fancy type leaves of plants that are de-eyed are variegated with variable areas that are dark green, light green, yellow green, red orange, whitish green and white in color; leaves of plants that are not de-eyed are mostly dark green in color with variable areas of variegation and interveinal areas with variably coalescing red orange and greyed purple-colored spots and splotches; and petioles that are tan pink in color with faint dark brown-colored streaks, stipples and tessellations.

4 Drawing Sheets

Botanical designation: *Caladium* X *hortulanum*.
Cultivar denomination: 'MESMERIZED'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'Mesmerized'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'RS-03-03', disclosed in U.S. Plant Pat. No. 26,265, as the female, or seed, parent with *Caladium* X *hortulanum* 'Twist N' Shout', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mesmerized'. These characteristics in combination distinguish 'Mesmerized' as a new and distinct *Caladium* plant:

1. Intermediate in height and upright plant habit; plants with tubers de-eyed are more compact and mounding; leaf petioles upright to outwardly leaning with development.
2. Vigorous growth habit and rapid growth rate.
3. Fancy type leaves of plants that are de-eyed are variegated with variable areas that are dark green, light green, yellow green, red orange, whitish green and white in color; leaves of plants that are not de-eyed are mostly dark green in color with variable areas of variegation and interveinal areas with variably coalescing red orange and greyed purple-colored spots and splotches.
4. Petioles that are tan pink in color with faint dark brown-colored streaks, stipples and tessellations.

Plants of the new *Caladium* differ primarily from plants of the female parent, 'RS-03-03', in the following characteristics:

1. Plants of the new *Caladium* have fancy type leaves whereas plants of 'RS-03-03' have strap (or lance) type leaves.
2. Plants of the new *Caladium* are taller than plants of 'RS-03-03'.
3. Plants of the new *Caladium* and 'RS-03-03' differ in leaf color as leaves of 'RS-03-03' are pearlescent white to greenish white in color with dark green-colored margins and white to greenish white-colored venation.

Plants of the new *Caladium* differ primarily from plants of the male parent, 'Twist N' Shout', in the following characteristics:

1. Plants of the new *Caladium* are denser than plants of 'Twist N' Shout'.
2. Leaves of plants of the new *Caladium* are flatter than and not as twisted as plants of 'Twist N' Shout'.
3. Plants of the new *Caladium* and 'Twist N' Shout' differ in leaf color as leaves of 'Twist N' Shout' are olive green in color with green to coppery bronze-colored venation and coppery orange-colored spots and blotches.

Plants of the new *Caladium* can be compared to plants of *Caladium* X *hortulanum* 'Highlighter', not patented. In side-by-side comparisons, plants of the new *Caladium* differ primarily from plants of 'Highlighter' in the following characteristics:

1. Plants of the new *Caladium* have fancy type leaves whereas plants of 'Highlighter' have strap (or lance) type leaves.
2. Plants of the new *Caladium* and 'Highlighter' differ in leaf color as leaves of 'Highlighter' are light green and dark green variegated.

Plants of the new *Caladium* can be compared to plants of *Caladium* X *hortulanum* 'Raspberry Moon', disclosed in U.S. Plant Pat. No. 20,069. In side-by-side comparisons, plants of the new *Caladium* differ primarily from plants of 'Raspberry Moon' in the following characteristics:

1. Plants of the new *Caladium* are shorter and more compact than plants of 'Raspberry Moon'.
2. Plants of the new *Caladium* and 'Raspberry Moon' differ in leaf color as leaves of 'Raspberry Moon' are lime green in color with random dark green and raspberry red-colored coalescing spots and splotches.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Mesmerized' in a container and grown in a shadehouse (tuber de-eyed).

The photograph at the top of the second sheet is a comparison view of typical potted plants of the female parent, 'RS-03-03' (left), 'Mesmerized' (center, tuber de-eyed) and the male parent, 'Twist N' Shout' (right).

The photograph at the bottom of the second sheet is a comparison view of typical potted plants of 'Highlighter' (left), 'Mesmerized' (center, tuber de-eyed) and 'Raspberry Moon' (right).

The photograph at the top of the third sheet is a comparison view of typical plants of 'Mesmerized' grown in containers; the plant on the left has not had its tuber de-eyed and the plant on the right has had its tuber de-eyed prior to planting.

The photograph at the bottom of the third sheet is a close-up view of typical freshly-harvested tubers with roots and leaf petioles of 'Mesmerized'.

The photograph on the fourth sheet is a close-up view of a typical inflorescence of 'Mesmerized' (tuber de-eyed).

DETAILED BOTANICAL DESCRIPTION

The aforementioned photographs and following observations and measurements describe plants grown in 15-cm containers in a polypropylene-covered shadehouse (50% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were seven weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Mesmerized'.

Parentage:

*Female, or seed, parent.*—*Caladium* X *hortulanum* 'RS-03-03', disclosed in U.S. Plant Pat. No. 26,265.

*Male, or pollen, parent.*—*Caladium* X *hortulanum* 'Twist N' Shout', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregularly ovate to rounded in shape. Height: About 3 cm. Diameter: About 5.5 cm to 7 cm. Segment height: About 2 cm. Segment diameter: About 1.9 cm. Texture: Thick, starchy; somewhat brittle. Color: Epidermis, freshly-harvested: Close to N170D. Epidermis, dried: Close to 200A to 200B. Cortical tissue: Close to 11D and 158D. Axillary buds: Close to 27D. Root description: Thick, fleshy contractile roots with few lateral branches; color, close to N155D. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Intermediate in height and upright plant habit; plants with tubers de-eyed are more compact and mounding in plant habit; vigorous growth habit and rapid growth rate; potted plants in finished or saleable form in about six to seven weeks after planting tubers; leaf petioles and leaves arise from one or more growing points on tubers; petioles mostly upright and outwardly leaning with development; inflorescences held above the foliar plane on strong upright scapes.

*Plant height, from soil level to top of foliar plane, shadehouse-grown potted plants, tubers not de-eyed.*—About 28 cm to 34 cm.

*Plant height, from soil level to top of inflorescences, shadehouse-grown potted plants, tubers not de-eyed.*—About 41 cm.

*Plant diameter or spread, shadehouse-grown potted plants, tubers not de-eyed.*—About 34 cm to 41 cm.

*Number of shoots per plant, shadehouse-grown potted plants, tubers not de-eyed.*—About two to three develop per #1 tuber.

*Number of shoots per plant, shadehouse-grown potted plants, tubers de-eyed.*—About four to five develop per #1 tuber.

*Cataphylls, shadehouse-grown potted plants.*—Length: About 6 cm to 9.3 cm. Width: About 1.5 cm to 2 cm. Shape: Deltoid or ligulate. Apex: Acute. Base: Sheathing the stem. Color, inner surface: Close to N155D; colors and patterns on the outer surface are visible on the inner surface. Color, outer surface: Close to N155C; streaked, stippled and tessellated with close to N200A; with development, color becoming closer to 199A and 200B and stained with close to 187B.

Leaf description:

*Arrangement and type.*—Alternate; simple; fancy type.

*Length, shadehouse-grown potted plants, tubers not de-eyed.*—About 24.2 cm to 25 cm.

*Width, shadehouse-grown potted plants, tubers not de-eyed.*—About 15 cm to 17 cm.

*Length, shadehouse-grown potted plants, tubers de-eyed.*—About 14.2 cm to 20 cm.

*Width, shadehouse-grown potted plants, tubers de-eyed.*—About 10 cm to 11.6 cm; when flattened, about 10.9 cm to 12.6 cm.

*Shape.*—Ovate.

*Apex.*—Acute.

*Base.*—Sagittate to peltate.

*Margin.*—Entire; wavy with broad undulations.

*Texture, upper and lower surfaces.*—Somewhat rugose, glabrous.

*Luster, upper surface.*—Dull sheen.

*Luster, lower surface.*—Slightly glaucous, dull sheen.

*Venation pattern.*—Pinnate.

*Color, shadehouse-grown potted plants, tubers de-eyed.*—Developing and fully expanded leaves, upper surface: Background: Variable variegated areas, close to 147A, 147C, 147D, 145B, 145C and 145D. Edge: Close to 187A. Basal notch: Close to 60A. Petiole attachment: About N186C. Midvein and primary venation: Variably variegated, close to 147A, 147C, 147D, 145B, 145C, 145D and 155D. Interveinal areas: Close to N34A. Random spots and splotches: Close to 147A, 147C, 147D, 145B, 145C and 145D. Developing and fully expanded leaves, lower surface: Background: Close to 191A and close to 191A tinged with close to 189A. Edge: Close to 187A to 187B. Basal notch: Close to 60A and 187C. Midvein: Close to 147D and close to 147C to 147D tinged with close to 177D. Primary venation: Close to 147B and close to 147B to 147C. Areas surrounding venation: Close to 155B, 157C and 157D. Interveinal areas: Close to N170D and close to lighter than 166D. Random spots and splotches: Close to 157D, 193A, 147B to 147C, 187B and 187C.

*Color, shadehouse-grown potted plants, tubers not de-eyed.*—Developing and fully expanded leaves, upper surface: Background: Close to 147A to 147B. Edge: Close to 187B. Basal notch: Close to 187A. Midvein and primary venation: Close to 147A. Interveinal areas: Variable variegated areas, close to 145D, 144D, 157A and 147B. Random spots and splotches: Close to 183A and N34A. Developing and fully expanded leaves, lower surface: Background: Close to 191A and close to 191A to 191B. Edge: Close to 187B to 187C. Basal notch: Close to 187A. Midvein: Close to 195B tinged with close to 177D; distally, close to 147D. Primary venation: Close to 194B, 147C and 147D. Interveinal areas: Close to N170C and N170D. Random spots and splotches: Close to 187A and close to 187A to 187B.

*Petioles.*—Aspect: Initially upright and straight; with development, somewhat outwardly leaning; flexible. Length, shadehouse-grown potted plants, tubers not de-eyed: About 23 cm to 28.4 cm. Diameter, distally, shadehouse-grown potted plants, tubers not de-eyed: About 4.5 mm to 5 mm. Diameter, proximally, shadehouse-grown potted plants, tubers not de-eyed: About 11 mm to 14 mm. Length, shadehouse-grown potted plants, tubers de-eyed: About 18 cm to 26 cm. Diameter, distally, shadehouse-grown potted plants, tubers de-eyed: About 3 mm to 4.5 mm. Diameter, proximally, shadehouse-grown potted plants, tubers de-eyed: About 6 mm to 8.5 mm. Texture: Smooth, glabrous. Color, shadehouse-grown potted plants: Close to 182D and N170D faintly streaked, stippled and tessellated with close to 200D; below the leaf and petiole junction, close to 182D faintly streaked, stippled and tessellated with close to 200D; proximally, close to 147B and close to 147C to 147D. Wing length, shadehouse-grown potted plants: About 4 cm to 7.4 cm. Wing diameter, shadehouse-grown potted plants: About 7 mm to 9 mm. Texture and luster, inner and outer surfaces: Smooth, glabrous; dull. Wing color, shadehouse-grown potted plants: Inner surface: Close to N155D; colors and patterns on the outer surface are visible on the inner surface. Outer surface: Close to 155C, N155C and 147C variably tinged with close to 36C and 36D and stippled, streaked and tessellated with close to 147B tinged with close to N200A.

Inflorescence description: Inflorescences observed on five week-old shadehouse-grown potted plants.

*Inflorescence arrangement.*—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; sweet, jasmine-like with camphor note.

*Natural flowering season and flower longevity*.—Plants of the new *Caladium* typically flower during the spring in central Florida; flowers develop about four to five weeks after growth commences; inflorescences last about three days before fading; inflorescences persistent.

*Spathe*.—Length, overall: About 13 cm. Length, distal open portion: About 9.1 cm. Length, proximal closed portion: About 3.9 cm. Width, distal open portion: About 3.8 cm. Depth, distal open portion: About 3.1 cm. Width, at constriction: About 2 cm. Width, proximal closed portion: About 3.8 cm. Shape, open portion: Obovate. Apex: Acuminate. Base: Acute to obtuse. Margin: Entire. Texture, front and rear surfaces: Smooth, glabrous. Luster, front surface: Dull sheen. Luster, rear surface: Dull sheen; proximally, glaucous. Color, front surface: Distal open portion: Close to 155C tinged with close to 157B to 157C; color becoming closer to 199C to 199B with development. Proximal closed portion: Close to 147C; towards the base, faintly flushed with close to N186C; color does not change with development. Color, rear surface: Distal open portion: Close to 149D, 145C and 157C; color becoming closer to 199C to 199B with development. Proximal closed portion: Close to 147B and 147C and flushed with close to 146C; color does not change with development.

*Spadix*.—Length, overall: About 10.5 cm. Length, male flower zone: About 6.2 cm. Length, sterile zone: About 2.3 cm. Length, female flower zone: About 2 cm. Diameter, male flower zone: About 1.1 cm. Diameter, sterile flower zone: About 7 mm. Diameter, female flower zone: About 1 cm. Shape: Columnar, spindle-shaped. Apex: Acuminate. Base: Obtuse. Aspect: Upright. Color, mature, male zone: Close to 155C. Color, mature, sterile zone: Close to 155C. Color, mature, female zone: Close to 158D and 38D. Male flowers: Quantity per spadix: About 182. Shape: Obovate. Height: About 3.5 mm. Diameter: About 4 mm. Pollen amount: Abundant. Pollen color: Close to 4C. Female flowers: Quantity per spadix: About 168. Shape: Obovate. Height: About 2.5 mm. Diameter: About 2 mm. Stigma color: Close to 158D. Ovary color: Close to 38D.

*Scape*.—Length: About 28 cm. Diameter: About 7 mm. Strength: Sturdy; flexible. Aspect: Mostly erect. Texture and luster: Smooth, glabrous; dull sheen; distally, glaucous. Color: Close to 147C faintly streaked and stippled with close to 199A; distally, close to 147B faintly stippled and streaked with close to 199A.

*Seeds and fruits*.—To date, seed and fruit development have not been observed on plants of the new *Caladium*.

Disease & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Mesmerized' as illustrated and described.

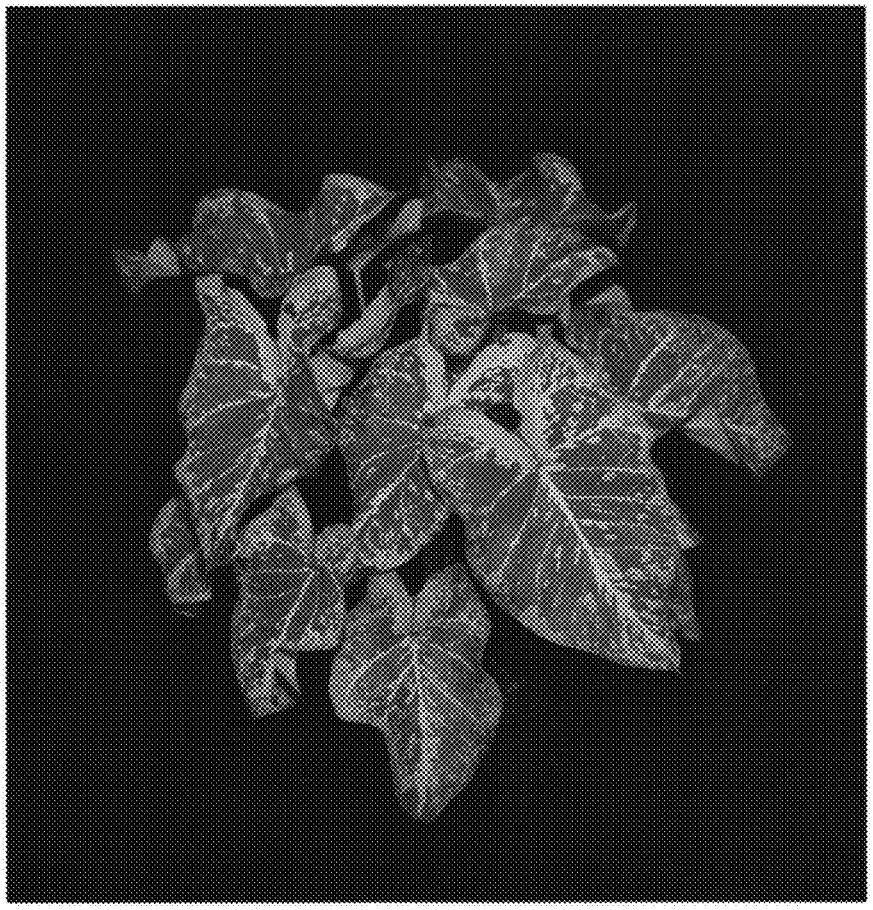

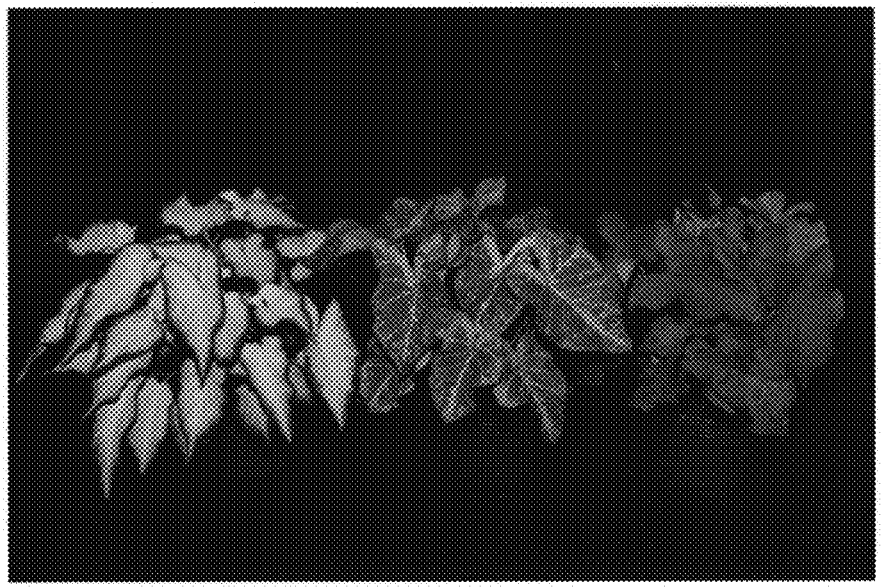
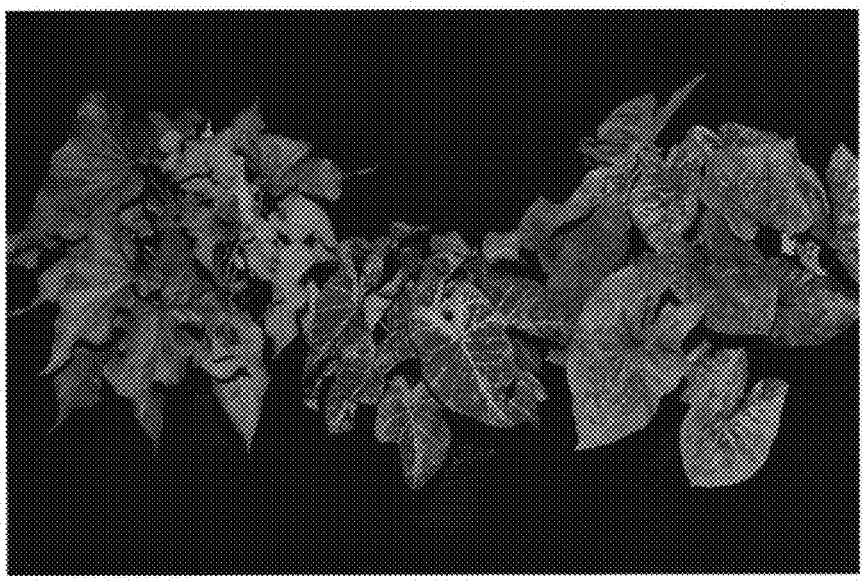

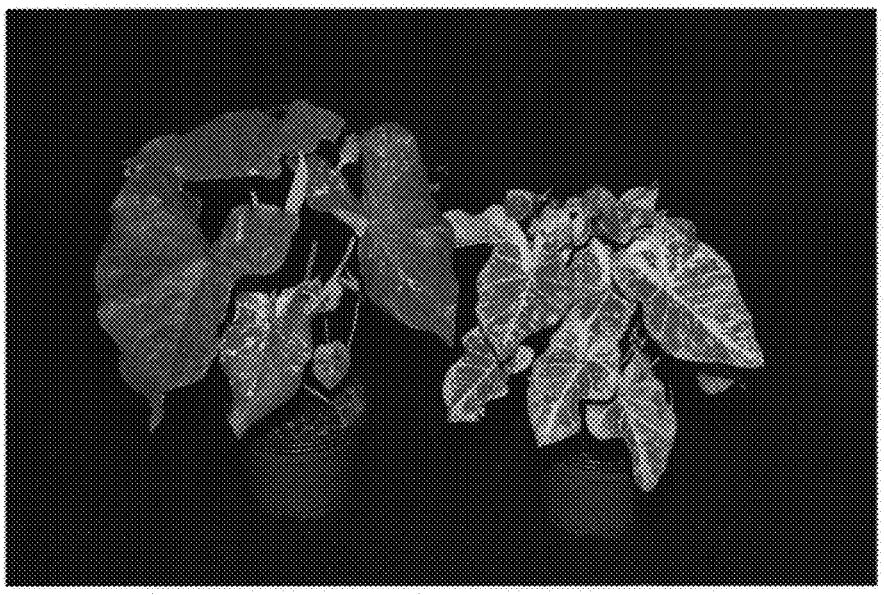
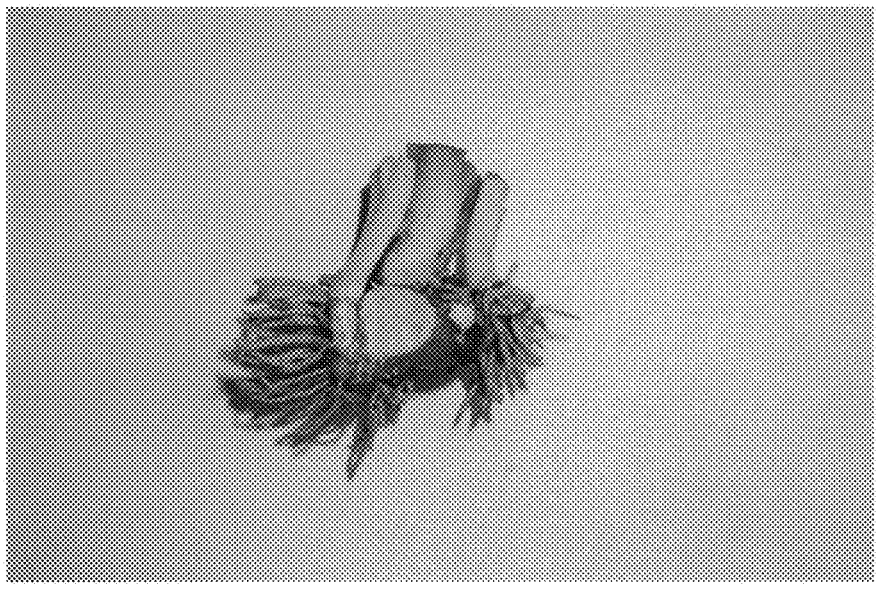

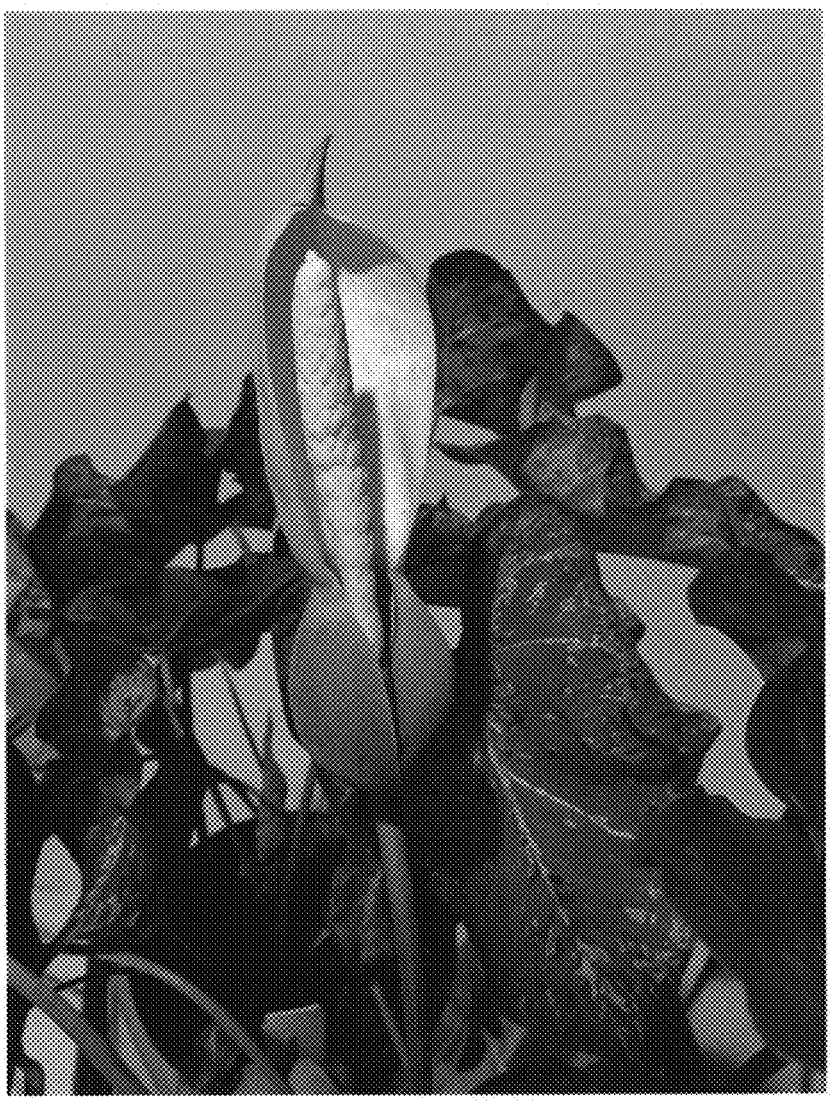

* * * * *